United States Patent [19]
Vitale

[11] Patent Number: 5,683,466
[45] Date of Patent: Nov. 4, 1997

[54] JOINT SURFACE REPLACEMENT SYSTEM

[76] Inventor: Glenn C. Vitale, 1 Peck Ave., Unit #2, West Haven, Conn. 06516

[21] Appl. No.: 622,031

[22] Filed: Mar. 26, 1996

[51] Int. Cl.$^6$ .................................................. A61F 2/42
[52] U.S. Cl. ........................................ 623/18; 62/21
[58] Field of Search ........................ 623/16, 18, 20, 623/22, 23; 606/72, 75

[56] References Cited

U.S. PATENT DOCUMENTS

| | | |
|---|---|---|
| 2,696,817 | 12/1954 | Prevo . |
| 2,952,254 | 9/1960 | Keating .................................. 606/75 |
| 3,648,294 | 3/1972 | Shahrestani .......................... 623/22 |
| 3,681,786 | 8/1972 | Lynch . |
| 3,685,058 | 8/1972 | Tronzo ................................... 623/22 |
| 4,085,466 | 4/1978 | Goodfellow et al. . |
| 4,332,036 | 6/1982 | Sutter et al. .......................... 623/18 |
| 4,355,429 | 10/1982 | Mittelmeier et al. . |
| 4,385,404 | 5/1983 | Sully et al. ............................ 623/18 |
| 4,462,120 | 7/1984 | Rambert et al. . |
| 4,642,122 | 2/1987 | Steffee . |
| 4,725,280 | 2/1988 | Laure . |
| 4,728,330 | 3/1988 | Comparetto ........................... 623/18 |
| 4,759,768 | 7/1988 | Hermann et al. . |
| 4,796,612 | 1/1989 | Reese ..................................... 606/72 |
| 4,955,916 | 9/1990 | Carignan et al. . |
| 4,976,740 | 12/1990 | Kleiner ................................... 623/18 |
| 4,988,351 | 1/1991 | Paulos et al. .......................... 606/72 |
| 5,007,932 | 4/1991 | Bekki et al. . |
| 5,037,440 | 8/1991 | Koenig . |
| 5,092,896 | 3/1992 | Meuli et al. ............................ 623/21 |
| 5,176,710 | 1/1993 | Hahn et al. . |
| 5,207,712 | 5/1993 | Cohen . |

*Primary Examiner*—David Isabella
*Attorney, Agent, or Firm*—Bachman & LaPointe, P.C.

[57] ABSTRACT

The present invention relates to an articular joint replacement system. The system has first and second components. Each component has a tapered head piece for covering the end of a bone and for acting as an articular surface, an integrally formed screw stem having a length sufficient to extend into the medullary canal, and inwardly angled bone grips affixed to the underside of the head piece to allow solid fixation to the bone by compression press fit. The head piece of the first component is provided with a shaped exterior surface which complements the shaped exterior surface of the head piece of the second component and which allows motion in three planes.

24 Claims, 3 Drawing Sheets

JOINT SURFACE REPLACEMENT SYSTEM

BACKGROUND OF THE INVENTION

The present invention relates to an articular system for replacing the cartilaginous surface in a human joint.

The use of prosthetic devices to replace joints and various bone and cartilage structures in a human body is well known in the prior art. These devices have taken a wide variety of configurations and shapes which are often closely related to the particular joint or anatomical structure being replaced. Described below are some of various devices shown in the patent literature.

U.S. Pat. Nos. 3,681,786 to Lynch, 4,725,280 to Laure, 4,759,768 to Hermann et al., 4,955,916 to Carignan et al., and 5,007,932 to Bekki et al. illustrate prosthetic devices designed to replace human finger joints. The Lynch patent relates to a prothesis formed from a single piece of flexible elastomeric, physiologically inert material and a polyester felt pad embedded within the prothesis. The felt pad has an exposed surface which provides for the ingrowth of body tissue. The one piece prosthesis is radiated to provide areas of different flexibility.

The Laure patent illustrates a prosthetic joint adopted to replace either the proximal or distal phalangeal joint of the finger. The joint includes a shell-like member secured to the distal end of one phalanx and a tack portion which extend into the other phalanx. The shell has a transverse cross section which results in two convex bearing surfaces and the tack portion has a head provided with a concave bearing surface.

The Hermann et al. patent illustrates a prosthetic joint comprising two pins each designed to be directly or indirectly inserted into a respective one of the two bones to be joined. Articulation surfaces are provided between the pins.

The Carignan et al. patent illustrates a thumb joint prosthesis having carpal and metacarpal components which are tapered and threaded to facilitate fixation. The carpal component has a U-shaped cavity containing a polyethylene insert which receives the spherical end of a tapered head which is received in a corresponding cavity within the metacarpal component.

The Bekki et al. patent illustrates a two member prosthetic device where the first member has a convex curved surface and the second member has a concave curved surface which is in sliding contact with the convex curved surface. A boss is provided to limit the sliding movement of the joint.

U.S. Pat. No. 2,696,817 to Prevo illustrates a prosthetic elbow joint comprising two finned shafts insertable into the marrow cavities of the humerus and the ulna, which shafts are pivotally connected by a trunnion.

U.S. Pat. Nos. 4,355,429 to Mittlemeier et al., 4,462,120 to Rambert et al., 4,085,466 to Goodfellow et al. and 5,176,710 to Hahn et al. illustrate various knee prosthetic devices. The Mittlemeier et al. patent illustrates a slide prothesis which includes a surface replacement for the knee cap having anchoring pins which are provided with a saw tooth-like or bone screw-shaped profile.

The Rambert et al. patent illustrates a total knee prosthesis having upper and lower support members provided with externally threaded, tapered shanks to which they are detachably secured. The shanks are screwable into the medullary canals of the femur and the tibia.

The Goodfellow et al. patent illustrates a device having first and second components respectively providing convex and relatively flat articulatory bearing surfaces. A third component is locate between the two other components.

The Hahn et al. patent illustrates a prosthetic device made from materials having a low bulk modulus of elasticity.

U.S. Pat. Nos. 4,642,122, to Steffee and 5,037,440 to Koening illustrate devices for replacing a toe joint. The Steffee device comprises a one-piece tack member implantable into the distal end of a metatarsal and a one-piece socket member implantable into the proximal end of a phalanx. The tack member has an enlarged head defining a part-spherical convex surface which engages a part-spherical concave bearing surface on an enlarged head of the socket member.

The Koenig patent illustrates a device similar to Steffee. Koenig's device also includes a first member having a convex surface and a second member having a concave surface.

U.S. Pat. No. 5,207,712 to Cohen illustrates an absorbable joint implant for lesser digits and metatarsal phalangeal joints. The implant includes shafts and a control spacer which are inserted into holes in the bones.

Commercial toe implants are sold by companies such as Johnson & Johnson, Kinetikes Medical, Inc., Micro Aire Surgical Instruments, Dow Corning and Sutter Biomedical, Inc. The structure of these implants are described in a number of promotional materials which are set forth in an invention disclosure statement accompanying the instant application.

Many of the commercially available implants deteriorate, collapse, break and Suffer torque deformation. Additionally, implantation of some devices require modifications to the sub-chondral bone. Still further, some devices require the use of silicone, silastics, glues, ingrowth jackets, and grommets. These disadvantages are overcome by the joint replacement system of the present invention.

SUMMARY OF THE INVENTION

Accordingly, it is an object of the present invention to provide a significantly improved joint surface replacement system. Which replaces only the anatomical structure of cartilage.

It is a further object of the present invention to provide a joint surface replacement system that eliminates breakage, bulk and excessive weight—the major contributory factors which lead to destructive lateral shearing forces resulting in complete implant failure.

It is a further object of the present invention to provide a joint surface replacement system as above that provides a full range of motion in three planes.

It is still a further object of the present invention to provide a joint surface replacement system as above which is firmly anchored to bone.

It is yet a further object of the present invention to provide a relatively simple method for installing the joint surface replacement system of the present invention making it extremely cost effective.

The foregoing objects are achieved by the joint surface replacement system and the installation method of the present invention.

In accordance with the present invention, the joint surface replacement system of the present invention has two elements which are each implanted into one of the bones forming the joint. The two elements define the new joint surfaces. A first one of the elements has a partially spherical member for covering an end of a first one of the bones, a centrally located screw means formed integrally with the partially spherical member and a means for gripping the end of the first bone for allowing solid fixation by compression press fit. The second one of the elements has a structure substantially identical to that of the first one of the elements. It too has a partially spherical member for covering an end of the second bone, an integral screw means and a bone end gripping means. The second element differs from the first element only by the shape of the partially spherical member. The second element has a partially spherical member with an outer surface shaped to mate with the outer surface of the partially spherical member of the first element. In a preferred embodiment, the first element has a partially spherical member with a convexly shaped outer surface, while the second element has a partially spherical member with a concavely shaped outer surface.

It has been found that the joint surface replacement system of the present invention offers numerous advantages. For example, the joint surface replacement system is formed from low-mass components which eliminates breakage, bulk and excessive weight. The joint surface replacement system replaces only the area of anatomic cartilage by size and function and provides full range of motion in all three planes. The joint surface replacement system also completely eliminates detritic synovitis.

Other details of the joint surface replacement system of the present invention as well as other objects and advantages attendant thereto are set forth in the following detailed description and the accompanying drawings in which like reference numbers depict like elements.

DETAILED DESCRIPTION OF THE PREFERRED EMBODIMENT(S)

Figure 1:
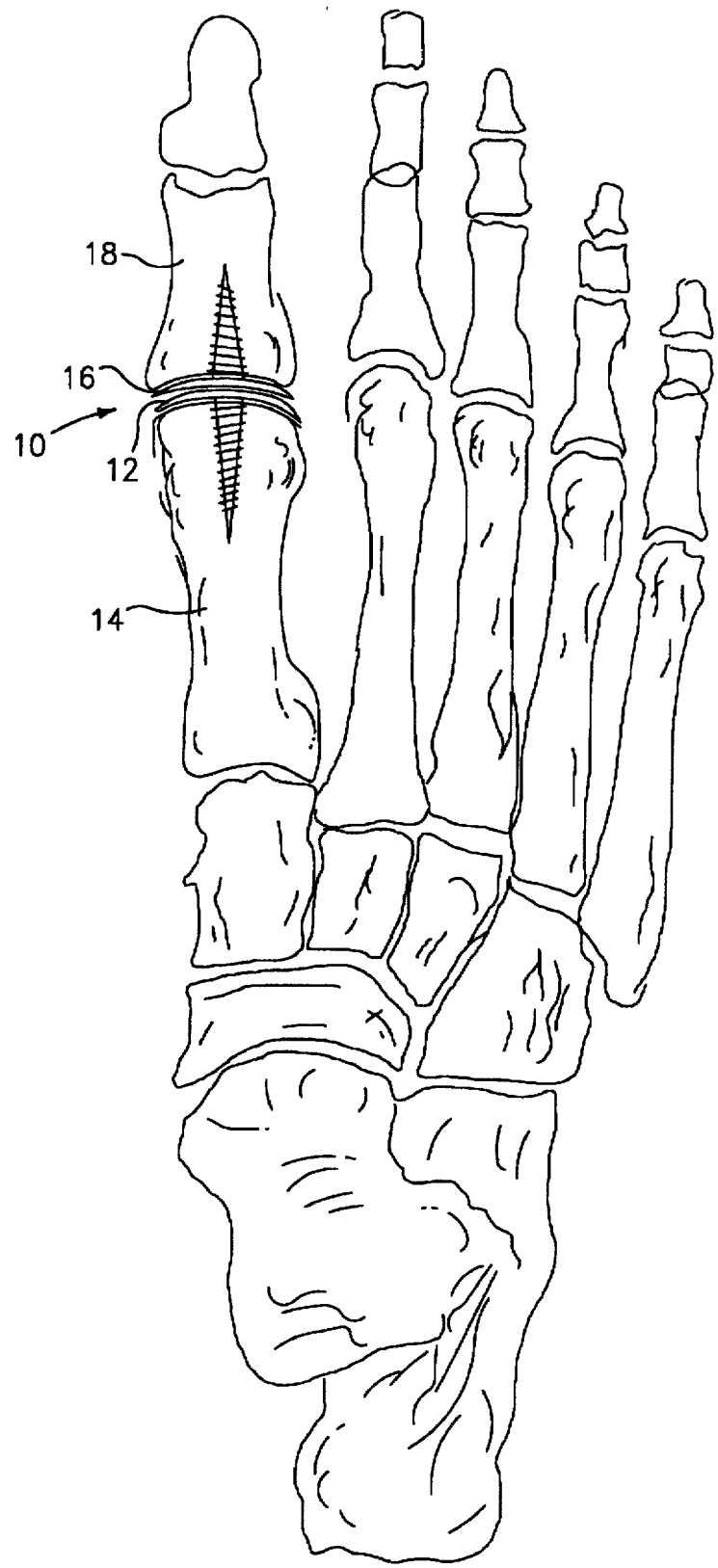
FIG. 1 is a dorsal-plantar view of a human foot showing a total first metatarsal phalangeal joint articular surface replacement using the joint surface replacement system of the present invention.
Figure 2:
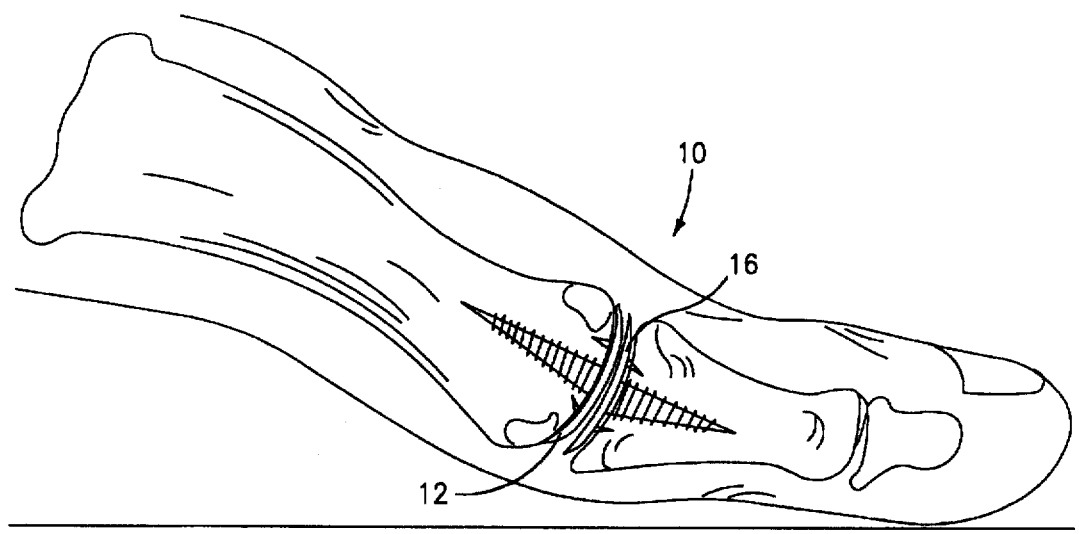
FIG. 2 is a sagittal view of the foot of FIG. 1 illustrating the joint surface replacement system of the present invention.

Referring now to the drawings, FIGS. 1 and 2 illustrate a total first metatarsal phalangeal articular surface replacement using the joint surface replacement system 10 of the present invention. As shown in these figures, the system 10 is formed by a first component 12 implanted into a first bone 14 and a second component 16 implanted into a second bone 18. The system 10 is designed to replace only the cartilaginous surface and to facilitate functioning to the original anatomic structures. The system of the present invention is believed to be a first of its kind.

Figure 3:
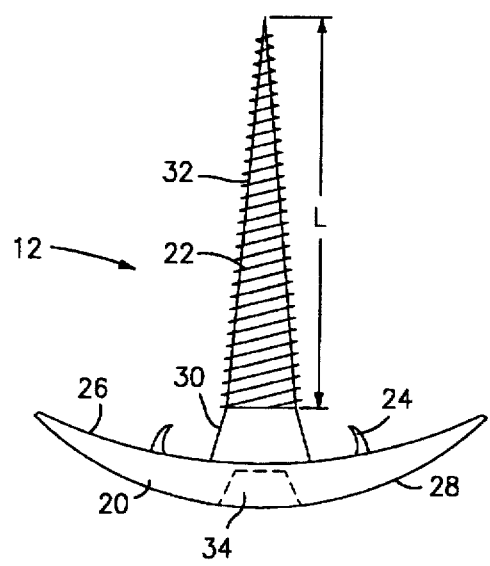
FIG. 3 is a side view of a first component of the joint surface replacement system of the present invention.
Figure 4:
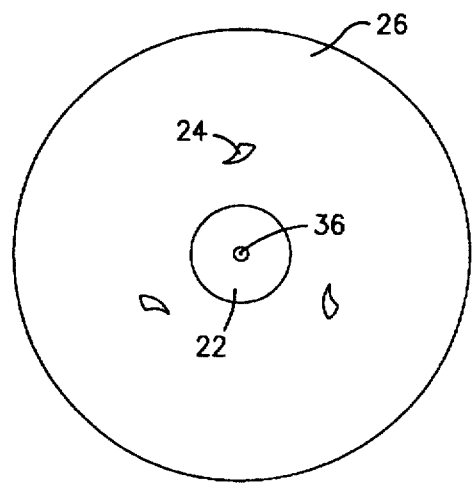
FIG. 4 is an end view of the first component of FIG. 3.

Referring now to FIGS. 3 and 4, the first component 12 is a uni-body structure having a partially spherical, tapered head piece 20 for covering the bone and functioning as an articular surface, an integrally formed cancellous screw stem 22, and a plurality of bone grips 24 integrally formed on the interior side 26 of the head piece 20. As can be seen from these figures, the interior and exterior surfaces 26 and 28 are each preferably convexly shaped. However, the two surfaces have different radii so as to form a tapered head piece with the thinnest portion being at the outer periphery of the head. For example, the center of the head piece may have a thickness of about 2.0 mm while the outer periphery has a thickness of about 1.0 mm. The screw stem 22 is preferably centrally located with respect to the head piece 20.

As shown in FIG. 3, the screw stem 22 has a non-threaded head portion 30 and a tapered threaded portion 32. The threaded portion has a length L sufficient to allow the first component to be inserted through the sub-chondral bone and into the medullary canal so as to substantially eliminate implant pistoning. Typically the length L will be from about 5 to about 15 millimeters. The non-threaded head portion 30 typically will have a length of about 3.5 millimeters. The thread on the portion 32 may have any suitable thread pattern and any suitable pitch.

The head piece 20 is preferably provided with a hexagonally shaped, tapered bore 34. The bore 34 is provided to accommodate a tool (not shown) for installing and removing the first component. The head piece 20 is dimensioned to allow it to fully cover the end of the bone in which it is inserted.

As shown in FIG. 4, the bone grips 24 are radially spaced about the center 36 of the head piece 20. Preferably, each of the bone grips 24 is spaced within the inner two-thirds of the bone in which the component is to be implanted, preferably from about 3 to about 4 mm from the center 36. While three bone grips 24 have been illustrated, it should be recognized that more than three bone grips can be provided. As shown in FIG. 3, the bone grips 24 are angled inwardly in relationship with the threads of the screw stem. The reason for this is to allow solid fixation by a compression press fit, thereby eliminating lateral stress forces in the transverse plane and rotational forces in the frontal plane. Preferably each bone grip has a length of about 2.0 mm.

The second component 16 is similar in construction to the first component 12. It too has a uni-body construction with a partially spherical, tapered head piece 40, a centrally positioned cancellous screw 42 and a plurality of bone grips 44 formed integrally with the interior surface 46 of the head piece 40. The head piece 40 is dimensioned so as to fully cover the end of the bone into which the second component 14 is implanted. The head piece is provided with a centrally located bore 48 for accommodating a tool (not shown) for installing and removing the second component.

Figure 5:
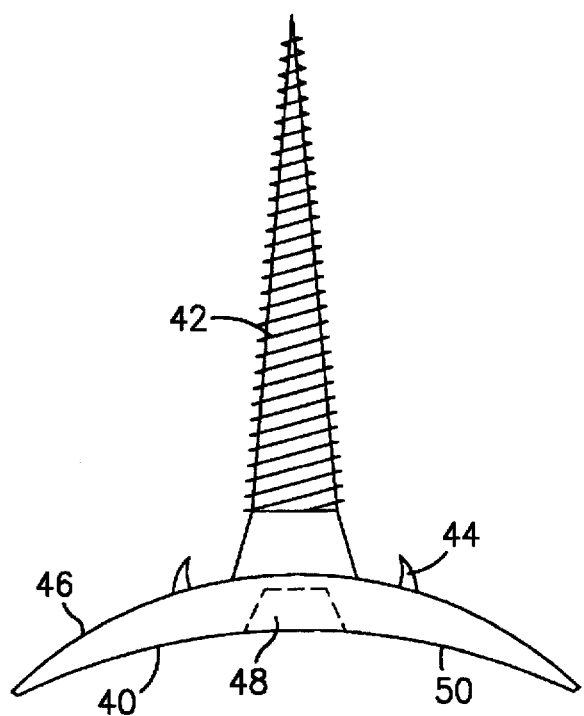
FIG. 5 is a side view of a second component of the joint surface replacement system of the present invention.
Figure 6:
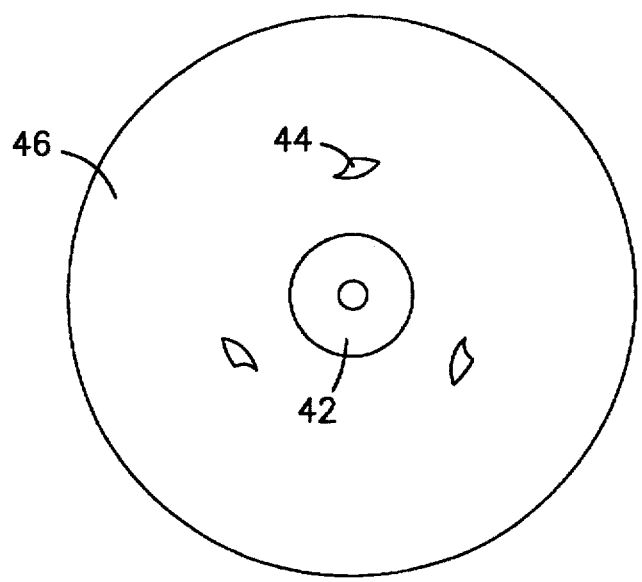
FIG. 6 is an end view of the second component of the joint surface replacement system of the present invention.

The head piece 40 differs from the head piece 34 of the first component 12 only by its shape. As shown in FIG. 5, the head piece 40 has concavely shaped interior and exterior surfaces 46 and 50 respectively so as to allow the head piece 40 to mate with the head piece 34 and provide motion in all three planes. As before, the inner and outer surfaces 46 and 50 are formed by different radii so as to form a tapered construction having its thinnest portion at its outer periphery.

The dimensions set forth for the first component may be used for the second component. The components 12 and 16 are preferably formed from low-mass materials. For example, the components may be formed from chromium alloys such as a chromium cobalt alloy, titanium, a titanium alloy or stainless steel. The use of these materials eliminates breakage, bulk and excessive weight—major contributory factors to increased lateral shearing forces, the leading cause of decreased longevity and failure.

In a preferred embodiment of the present invention, the interior surfaces 24 and 46 of the head pieces 20 and 40 are coarsely finished to allow for boney ingrowth and to facilitate fixation. Additionally, each of the bone grips 24 and 44 are provided with coarse surfaces which also allow for bone ingrowth and to facilitate fixation to the bone.

The joint surface replacement system is believed to be the first to be designed to replace only the function of cartilage, not the function of a metatarsal, phalangeal, femoral or humeral head. The partially spherical shape to the head pieces serves to replace the area of anatomic cartilage by size and function. The cancellous screw stem of each component eliminates pistoning forces and wearing of the inner cortical wall which leads to slippage and failure. The screw stem also allows easy removal when indicated and provides reliable stability and compression. The taper to the outer spherical screw head barrel allows each component to be anchored to the bone via insertion and joint use compression over time to press fit into bone. It also eliminates lateral shearing forces in both the transverse and sagittal planes, thus relieving the entire screw stem form abnormal forces. The angled bone grips are designed at the same thread angle to engage sub-chondral bone during the last one-quarter turn of compression fit during insertion of each component. The bone grips further anchor the respective component to bone during joint use while weight bearing.

The joint surface replacement system of the present invention is easily and clearly viewed on radiographs for observation and follow-up. The uni-body design of the system components allows a total view of the position of the entire implant.

The joint surface replacement system is quite advantageous from an anatomic standpoint. By limiting the articular replacement preparation to a standard first metatarsal phalangeal joint cheilectomy, the sub-chondral bone is left intact, thereby maintaining length and joint function of shock absorption and proprioception. Additionally, symmetry is preserved to that of the contralateral side. With respect to soft tissues, periarticular tendon, capsule and ligamentous structures are left intact during implantation of the system of the present invention. Soft tissue release and/or tendon transfer is utilized for joint alignment only, not for insertion of the implant articular replacement. Still further, the dorsal synovial sac may be preserved.

The system of the present invention eliminates detritic synovitis. No silicone, no silastics, no glues, no ingrowth jackets and no grommets, which cause abrasion shards are required. Additionally, there is no shearing fractures of the stem or articular surface materials. Still further, encapsulations of microfragments, bone erosions and fibrosis are eliminated, unlike other implants.

The articular surface replacement system of the present invention may be inserted at time of an osteotomy and may be used for primary or secondary fixation of a head osteotomy. It eliminates the need to heal the first osteotomy before performing the implantation procedure.

If desired, the head pieces of the components may be fabricated from a material different from the material used for the screw stem and the bone grips. For example, they may be fabricated from ceramic materials or high density polyethylene for situations where a hemi-joint or partial joint implantation is to be performed. A hemi-joint procedure would be performed where replacement of one articular surface alone is indicate. A partial joint procedure may be performed where only worn areas are to be replaced.

While the joint surface replacement system has been described in the context of replacing metatarsal phalangeal joints, it should be recognized that the same system could be used to replace other joints. For example, the system could be used to replace large joints such as hips and shoulders and digital joints of the fingers and toes.

The joint surface replacement system of the present invention may be installed by.

A. Performing the standard surgical approach for arthroplasty to the involved joint to be replaced through skin, superficial and deep tissues preserving vital structures and tendons;

B. Entering capsular structures through the usual incisional approach, as to expose the involved joint surfaces for replacement;

C. Performing the standard peripheral "Chielectomy" procedure when appropriate or indicated, preserving the dorsal sack and all subchondral bone;

D. Prepping subchondral bone and worn joint surfaces with a mirror image drill bit, containing a central guide hole drill bit to maintain position while drilling. Marking the centermost portion of the joint surface and placing a guide hole bit on the marked central area and beginning drilling until the entire bore just approaches joint surface and "mildly scouring" worn joint surface until evenly and shaped with the bore bit;

E. Drilling guide hole (length times width) to appropriate size of stem of implant;

F. Counter sinking subchondral bone and at guide hole site, for the seating of the screw head barrel;

G. Tapping guide hole for thread size of implant stem;

H. Grasping the unibody articular surface replacement unit with forceps and placing screw stem into tapped guide hole of bone. Utilizing a standard AO screwdriver, screw in entire articular surface replacement to compression against subchondral bone. Both screwhead barrel and bone grips will engage snugly into subchondral bone during final quarter to half compression turns of insertion;

I. Flushing entire wound with appropriate antibiotic flush;

J. Approximate and close capsule, deep tissues and superficial tissues in layers with absorbable sutures. At this point, optional tendon lengthening or transfers may be performed when indicated;

K. Closing skin in the usual fashion and apply post-operative dressing; and

L. Maintaining early post-operative range of motion exercise and immediate ambulation after first three days.

The articular surface replacement is designed to further press fit and compress as weight bearing in normal activity continues post-operatively and throughout life.

It is apparent that there has been provided in accordance with this invention a joint surface replacement system which fully satisfies the objects, means and advantages set forth hereinbefore. While the invention has been described in combination with specific embodiments thereof, it is evident that many alternatives, modifications and variations will be apparent to those skilled in the art in light of the foregoing description. Accordingly, it is intended to embrace all such alternatives, modifications and variations as fall within the broad scope of the appended claims.

What is claimed is:

1. An articular surface replacement system comprising:

a first component implanted into a first bone;

said first component having a partially spherical head piece dimensioned to cover an end of said first bone;

said first component having an integral, centrally located screw means for joining said first component to said bone, said screw means being affixed to an interior surface of said head piece and having a tapered threaded portion for allowing said first component to be anchored to the first bone;

said first component further having means for gripping said end of said bone and for allowing solid fixation by a compression press fit, said bone gripping means being integrally formed with said head piece and being radially spaced from the center of said head piece.

2. The system of claim 1 wherein said screw means has a non-threaded head portion adjacent said tapered threaded portion and said tapered threaded portion has a length sufficient to extend through intact sub-chondral bone and into the medullary canal in said first bone.

3. The system of claim 1 wherein said bone gripping means comprises a plurality of inwardly angled, radially spaced bone grips affixed to an interior surface of said head piece, each of said bone grips being located within the inner two-thirds of said bone and each of said bone grips having a coarsely finished surface which abuts said bone and which allows for ingrowth of said bone to further solidify fixation to the bone.

4. The system of claim 1 wherein said bone gripping means comprises at least three, tapered pin-shaped bone grips spaced about said interior surface of said head piece, said bone grips being equi-spaced from the center of said head piece and being angled inwardly toward an axis which passes through the center of said head piece.

5. The system of claim 1 wherein the head piece has an outer surface which forms a cartilaginous spherical articular surface and a coarsely finished interior surface for promoting boney ingrowth and thereby facilitating fixation.

6. The system of claim 1 wherein the head piece is tapered and is formed by an exterior surface having a radius of curvature different from a radius of curvature of an interior surface.

7. The system of claim 1 wherein said first component is formed from a material selected from the group consisting of titanium, a titanium alloy, stainless steel and a chromium alloy.

8. The system of claim 1 wherein said head piece has an outer surface covered by a ceramic material.

9. The system of claim 1 further comprising a second component implanted into a second bone, said second component having a partially spherically shaped head piece dimensioned to cover an end of said second bone, said head piece having an exterior surface shaped to mate with an exterior surface of said head piece of said first component and an interior surface which conforms to the shape of the end of said second bone.

10. The system of claim 9 wherein said head piece of said second component is concavely shaped and said head piece of said first component is convexly shaped so as to facilitate movement in three planes.

11. The system of claim 9 wherein said head piece of said second component has a tapered shape formed by said exterior surface having a radius of curvature and by an interior surface having a radius of curvature different from that of said exterior surface.

12. The system of claim 9 wherein said second component has a screw integrally formed with said head piece, said screw having a tapered threaded portion, and said tapered threaded portion having a length sufficient to extend through intact sub-chondral bone and into the medullary canal.

13. The system of claim 9 wherein said second component has means for gripping said second bone and for allowing solid fixation by a compression press fit.

14. The system of claim 13 wherein said bone gripping means comprises a plurality of radially spaced, pin-shaped bone grips affixed to an interior surface of said head piece, each of said bone grips being equally spaced from the center of said head piece and angled inwardly toward an axis which passes through the center of said head piece.

15. The system of claim 9 wherein said second component is formed from a material selected from the group consisting of titanium, titanium alloy, stainless steel and a chromium alloy.

16. The system of claim 9 wherein the head piece of said second component is covered by a ceramic material.

17. The system of claim 3 wherein said bone grips are designed to have a thread angle identical to a thread angle of said tapered threaded portion.

18. The system of claim 1 wherein said head piece has an outer surface covered by a high density polyethylene.

19. The system of claim 1 wherein said head piece, screw means and bone gripping means form a uni-body structure.

20. The system of claim 9 wherein the head piece of said second component is covered by a high density polyethylene material.

21. The system of claim 9 further comprising:

each of said head pieces having a centrally located bore for receiving a tool for inserting said components into and for removing said components from respective ones of said first and second bones without any destruction or resection of bone of any nature.

22. An articular surface replacement system comprising:

a first component to be inserted into a pre-drilled hole in a first bone;

a second component to be inserted into a pre-drilled hole in a second bone;

each of said first and second components comprising a uni-body construction having a head piece dimensioned to cover only an end of one of said first and second bones, an integrally formed centrally located screw having a tapered threaded portion for insertion into one of said pre-drilled holes in said first and second bones, and integrally formed inwardly angled, radially spaced, pin-shaped bone grips which penetrate into said end of one of first and second bones to anchor said respective one of said first and second components thereto; and said head piece of said first component having an arcuate shape and said head piece of said second component having a mating arcuate shape so that said components form a joint and permit motion in three planes.

23. The system of claim 1 further comprising:

said head piece of said first component covering only worn end areas of said first bone.

24. The articular surface replacement system of claim 22 further comprising:

said head piece of at least one of said first and second components covering only worn end areas of a respective one of said first and second bones.

* * * * *